US00PP27208P3

(12) United States Plant Patent
Braeunig

(10) Patent No.: US PP27,208 P3
(45) Date of Patent: Sep. 27, 2016

(54) ***PETUNIA* PLANT NAMED 'FLORTUNPIMORN'**

(50) Latin Name: *Petunia×hybrida*
Varietal Denomination: Flortunpimorn

(71) Applicant: Florensis B.V., Hendrik-Ido-Ambacht (NL)

(72) Inventor: Tobias Braeunig, Quedlinburg (DE)

(73) Assignee: Florensis B.V., Hendrik-Ido-Ambacht (NL)

( * ) Notice: Subject to any disclaimer, the term of this patent is extended or adjusted under 35 U.S.C. 154(b) by 0 days.

(21) Appl. No.: 14/545,608

(22) Filed: May 28, 2015

(65) Prior Publication Data

US 2016/0212911 P1 Jul. 21, 2016

Related U.S. Application Data

(60) Provisional application No. 62/125,383, filed on Jan. 20, 2015.

(51) Int. Cl.
*A01H 5/02* (2006.01)

(52) U.S. Cl.
USPC ..... Plt./356.1

(58) Field of Classification Search
USPC ..... Plt./356.1
See application file for complete search history.

*Primary Examiner* — Annette Para
(74) *Attorney, Agent, or Firm* — Audrey Charles

(57) ABSTRACT

A new and distinct cultivar of *Petunia* plant named 'Flortunpimorn', characterized by its pink and white bi-colored flowers, medium green-colored foliage, and moderately vigorous, compact, semi-upright growth habit, is disclosed.

1 Drawing Sheet

Latin name of genus and species of plant claimed: *Petunia×hybrida.*

Variety denomination: 'Flortunpimorn'.

BACKGROUND OF THE INVENTION

The present invention relates to a new and distinct cultivar of *Petunia* plant botanically known as *Petunia×hybrida* and hereinafter referred to by the cultivar name 'Flortunpimorn'.

The new cultivar originated in a controlled breeding program in Quedlinburg, Germany during May 2009. The objective of the breeding program was the development of *Petunia* cultivars with single-type flowers, unique flower coloration and patterns, and compact, semi-upright growth habit.

The new *Petunia* cultivar is the result of cross-pollination. The female (seed) parent of the new cultivar is the proprietary *Petunia×hybrida* breeding selection coded 4107-2, not patented, characterized by its light pink-purple colored flowers, medium green-colored foliage, and moderately vigorous, compact semi-upright growth habit. The male (pollen) parent of the new cultivar is the proprietary *Petunia×hybrida* breeding selection coded 4240-1, not patented, characterized by its white-colored flowers having a light pink star, medium green-colored foliage, and moderately vigorous, compact, upright growth habit. The new cultivar was discovered and selected as a single flowering plant within the progeny of the above stated cross-pollination during April 2010 in a controlled environment in Quedlinburg, Germany.

Asexual reproduction of the new cultivar by terminal stem cuttings since April 2010 in Quedlinburg, Germany; Arroyo Grande, Calif.; and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Flortunpimorn' as a new and distinct cultivar of *Petunia* plant:

1. Pink and white bi-colored flowers;
2. Medium green-colored foliage; and
3. Moderately vigorous, compact, semi-upright growth habit.

Plants of the new cultivar differ from plants of the female and male parents primarily in flower color and pattern and in having a more compact, semi-upright growth habit.

Of the many commercially available *Petunia* cultivars, the most similar in comparison to the new cultivar is Sweetunia Strawberry Morning 'Dueswebermo', U.S. Plant Pat. No. 21,672. However, in side by side comparisons, plants of the new cultivar differ from plants of 'Dueswebermo' in at least the following characteristics:

1. Plants of the new cultivar have a flower color pattern that is different from plants of 'Dueswebermo'; and
2. Plants of the new cultivar have an inner surface corolla tube color darker than plants of 'Dueswebermo'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Flortunpimorn'. The plants were grown in 4.5-inch pots for 9 weeks in a greenhouse in Arroyo Grande, Calif.

DETAILED BOTANICAL DESCRIPTION

Figure 1:
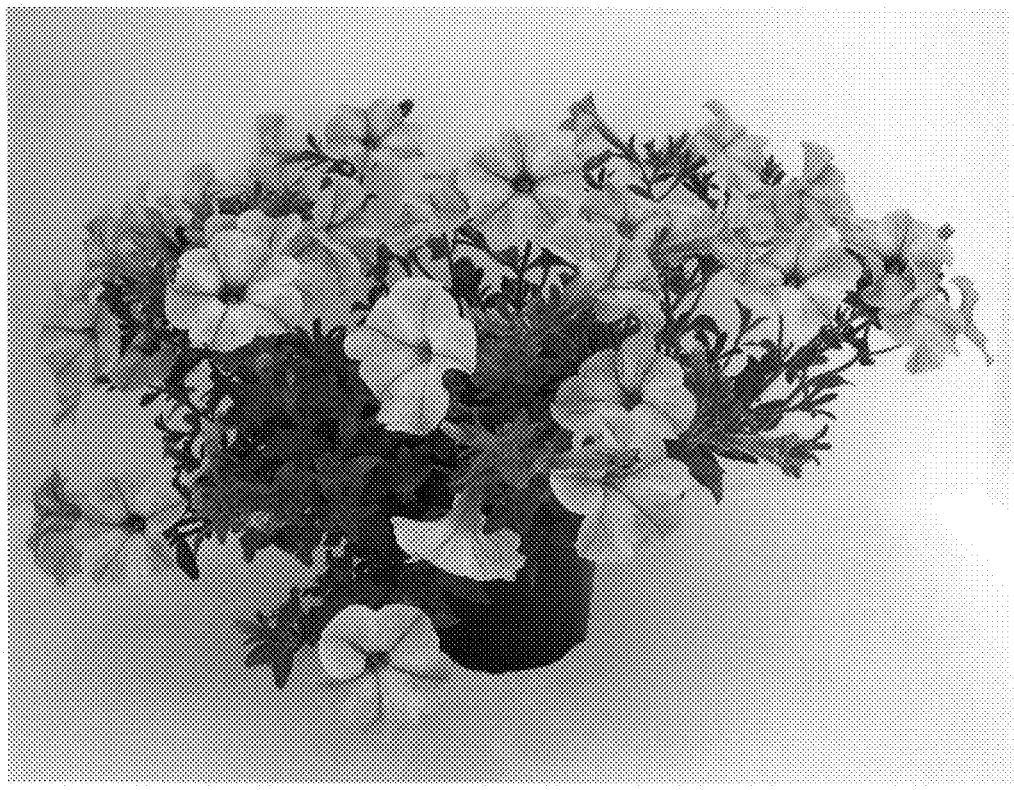
FIG. 1 illustrates a side view of the overall growth and flowering habit of 'Flortunpimorn'.
Figure 2:
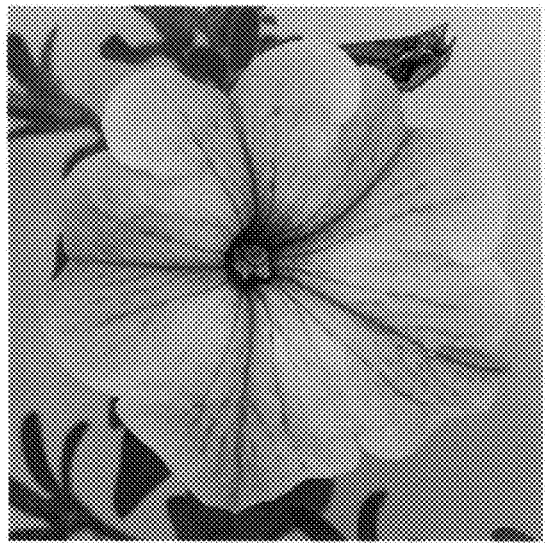
FIG. 2 illustrates a close-up view of an individual flower of 'Flortunpimorn'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2015 under natural light conditions in West Chicago, Ill.

The following descriptions and measurements describe plants produced from cuttings from stock plants and grown in a glass-covered greenhouse under conditions comparable to those used in commercial practice. The plants were grown in Arroyo Grande, Calif. in 4.5-inch pots for 9 weeks utilizing a soilless growth medium. Greenhouse temperatures averaged 65° F. (18° C.) during the day and approximately 50° F. (10° C.) during the night. No supplemental lighting was used. Measurements and numerical values represent averages of typical plants.

Botanical classification: *Petunia×hybrida* cultivar Flortunpimorn.

Parentage:

*Female parent*.—Proprietary *Petunia×hybrida* breeding selection coded 4107-2, not patented.

*Male parent*.—Proprietary *Petunia×hybrida* breeding selection coded 4240-1, not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Moderately vigorous, compact, semi-upright.

*Size*.—Height from soil level to top of plant plane: Approximately 19.0 cm. Width: Approximately 47.0 cm.

*Branching habit*.—Freely branching, pinching improves basal branching. Quantity of main branches per plant: Approximately 5.

*Branch*.—Strength: Moderate. Length: Approximately 19.5 cm. Diameter: Approximately 4.0 mm. Length of central internode: Approximately 1.9 cm. Texture: Densely glandular pubescent with a mixture of long and short hairs. Gland color: Colorless. Color of young and mature stems: 144A.

Foliage description:

*General description*.—Quantity of leaves per main branch: Approximately 16. Fragrance: Slight. Form: Simple. Arrangement on flowering stem: Opposite.

*Leaves*.—Aspect: Acute angle to stem. Shape: Ovate. Margin: Entire. Apex: Acute. Base: Attenuate. Venation pattern: Pinnate. Length of mature leaf: Approximately 3.2 cm. Width of mature leaf: Approximately 2.5 cm. Texture of upper and lower surfaces: Moderately glandular pubescent. Gland color: Colorless. Color of upper surface of young and mature foliage: 137A with venation of 144B to indistinguishable. Color of lower surface of young and mature foliage: Closest to 138B with venation of 144D to indistinguishable.

*Petiole*.—Length: Approximately 4.0 mm. Width: Approximately 3.0 mm. Texture: Densely glandular pubescent with a mixture of long and short hairs. Gland color: Colorless. Color: 144B.

Flowering description:

*Flowering habit*.—'Flortunpimorn' is freely flowering under outdoor growing conditions with substantially continuous blooming from spring through autumn and year-round in greenhouse environment.

*Lastingness of individual flower on the plant*.—Approximately 10 to 12 days.

Flower description:

*General description*.—Type: Simple, salverform. Quantity per plant: Approximately 54. Fragrance: Slight.

*Bud*.—Rate of opening: Generally takes 2 to 3 days for bud to progress from first color to fully open flower. Quantity per plant: Approximately 12.

*Bud just before opening*.—Shape: Oblong. Length: Approximately 3.6 cm. Diameter at apex: Approximately 7.0 mm. Diameter at base: Approximately 3.0 mm. Texture: Densely glandular pubescent. Gland color: Colorless. Color of petals: NN155A with venation of N137D. Color of tube: 145C with venation of N137D and 144A and 146A.

*Corolla*.—Diameter: Approximately 5.6 cm.

*Petals*.—Quantity: 5, fused to form a tube. Shape: Obovate. Appearance: Dull. Margin: Entire, wavy. Apex: Acute. Length from tube: Approximately 2.5 cm. Length of free portion: Approximately 1.3 cm. Width: Approximately 3.0 cm. Texture of upper surface: Glabrous. Texture of lower surface: Sparsely glandular pubescent. Gland color: Colorless. Color of upper surface when first open: NN155D with an overlay of 68B to 68A streaked with 70B, overlay color more intense surrounding midveins, midveins of N77A. Color of lower surface when first and fully open: NN155D lightly tinted with 68B, midveins of closest to 144A. Color of upper surface when fully open: NN155D with an overlay of 68B to 68A faintly streaked with 70B, overlay color more intense surrounding midveins, midveins of closest to but lighter than N77A.

*Corolla tube*.—Length: Approximately 3.2 cm. Diameter at distal end: Approximately 1.0 cm. Diameter at proximal end: Approximately 3.0 mm. Texture of inner surface: Glabrous. Texture of outer surface: Densely glandular pubescent. Gland color: Colorless. Color of inner surface: NN155A with a heavy overlay of N79A, venation of N77A. Color of outer surface: NN155A with a heavy overlay of N79A and venation of 146A.

*Sepals*.—Quantity per flower: 5, fused at base. Shape: Linear. Apex: Acute. Length: Approximately 1.8 cm. Width: Approximately 4.0 mm. Texture of upper and lower surfaces: Densely glandular pubescent. Gland color: Colorless. Color of upper surface: 137A. Color of lower surface: 137B transitioning to 144A at base.

*Peduncle*.—Strength: Strong, flexible. Aspect: Acute angle to stem. Length: Approximately 2.1 cm. Diameter: Approximately 2.0 mm. Texture: Densely glandular pubescent with a mixture of long and short hairs. Gland color: Colorless. Color: 144A.

*Reproductive organs*.—Androecium: Stamen quantity: 5, basifixed. Stamen length: Approximately 2.2 cm. Filament length of fixed portion: Approximately 1.0 mm. Filament color: NN155A. Anther shape: Bilobed. Anther length: Approximately 1.0 mm. Anther color: 156D with N79A where filament attaches. Pollen amount: Abundant. Pollen color: 155D. Gynoecium: Pistil quantity: 1 per flower. Pistil length: Approximately 2.3 cm. Stigma shape: Funnel. Stigma length: Approximately 1.0 mm. Stigma color: 146D with funnel portion tinted with N79A. Style length: Approximately 1.8 cm. Style color: 145C. Ovary length: Approximately 4.0 mm. Ovary color: 144A.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Flortunpimorn', substantially as herein illustrated and described.

* * * * *